United States Patent [19]

Marker et al.

[11] Patent Number: 5,744,645
[45] Date of Patent: Apr. 28, 1998

[54] TWO-STAGE PROCESS FOR PRODUCING DIISOPROPYL ETHER USING CATALYTIC DISTILLATION

[75] Inventors: Terry L. Marker, Warrenville; Gregory A. Funk, Carol Stream; Paul T. Barger, Arlington Heights; Harold U. Hammershaimb, Western Springs, all of Ill.

[73] Assignee: UOP, Des Plaines, Ill.

[*] Notice: The term of this patent shall not extend beyond the expiration date of Pat. No. 5,504,258.

[21] Appl. No.: 625,859

[22] Filed: Apr. 1, 1996

Related U.S. Application Data

[63] Continuation-in-part of Ser. No. 311,993, Sep. 26, 1994, Pat. No. 5,504,258.

[51] Int. Cl.$^6$ ..................................................... C07C 41/00
[52] U.S. Cl. ............................................................. 565/695
[58] Field of Search ............................................... 565/695

[56] References Cited

U.S. PATENT DOCUMENTS

| | | | |
|---|---|---|---|
| 4,935,552 | 6/1990 | Child et al. | 568/695 |
| 5,144,086 | 9/1992 | Harandi et al. | 568/698 |

*Primary Examiner*—Paul J. Killos
*Attorney, Agent, or Firm*—Thomas K. McBride; Eugene I. Snyder; Maryann Maas

[57] ABSTRACT

A process for the efficient production of diisopropyl ether where catalytic distillation is used to increase the yield of product beyond thermodynamic equilibrium limitations has been developed. In a hydration zone the propylene in a feedstock is reacted with water in the presence of a catalyst to effect hydration to produce an effluent stream containing at least water, unreacted propylene, and isopropyl alcohol, and then, in an etherification zone, at least a portion of the effluent stream is further reacted by catalytic distillation in the presence of a catalyst to effect reaction of propylene and isopropyl alcohol to form diisopropyl ether while concurrently separating an organic portion containing the diisopropyl ether and an aqueous portion, and collecting the organic portion containing the diisopropyl ether.

18 Claims, 1 Drawing Sheet

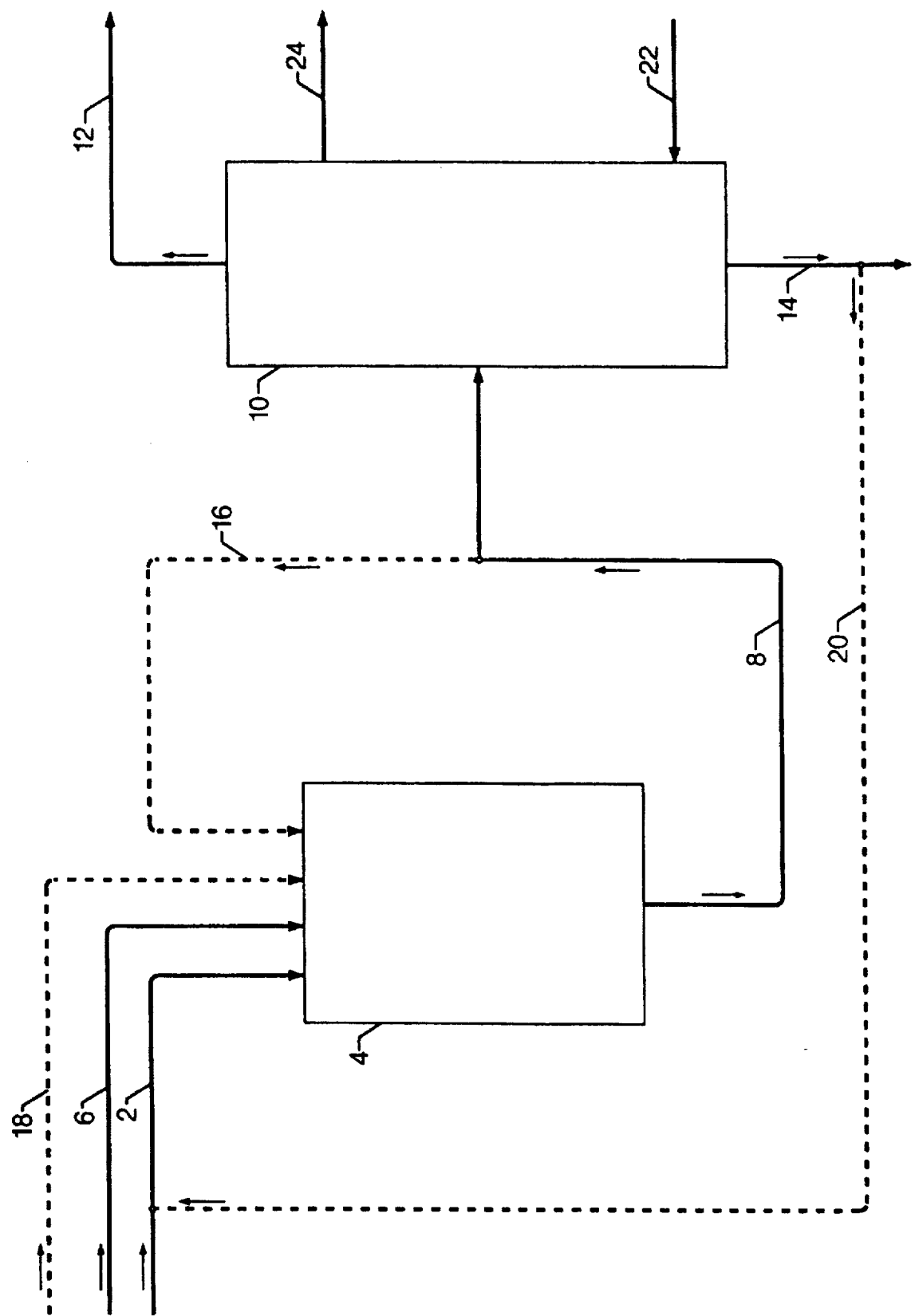

& 1

TWO-STAGE PROCESS FOR PRODUCING DIISOPROPYL ETHER USING CATALYTIC DISTILLATION

CROSS REFERENCE TO RELATED APPLICATION

This application is a continuation-in-part of our application Ser. No. 08/311,993 filed Sep. 26, 1994, now U.S. Pat. No. 5,504,258 all of which is hereby incorporated by reference.

BACKGROUND OF THE INVENTION

As tetraethyl lead is phased out, oxygenates have become more important in the petroleum refining industry as a source of gasoline octane boosters. The most common oxygenates for this purpose are the dialkyl ethers, and especially those in the $C_5$ to $C_7$ range. One such dialkyl ether that is generating much interest is diisopropyl ether (DIPE). DIPE is in the boiling range of gasoline, has a high blending octane number, and one reactant generally used in the formation of DIPE, propylene, is a by-product commonly available in refineries. The preparation of DIPE from propylene chemically proceeds by two sequential reactions, where propylene is first hydrated to isopropyl alcohol (IPA) (1) followed by reaction of the alcohol with the olefin (2) or bimolecular dehydration reaction of the alcohol (3) (Williamson synthesis) according to the equations,

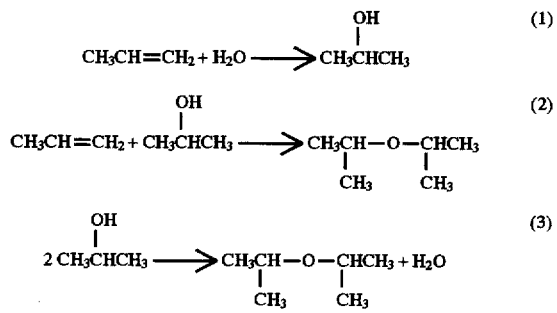

Hydration reactions such as reaction (1) are generally more difficult to perform than the etherification reaction (2) and the dehydration reaction (3). For example, severe conditions such as pressures as high as 500 to 1500 psig are required for hydration since in their normal states propylene is a gas and water is a liquid and the solubility of propylene in water is small. Therefore, the production rate of isopropyl alcohol by reaction (1) limits the rate of the overall sequence. Maximum overall production rate is achieved when the etherification is substantially accomplished by reaction (2) since reaction (2) only consumes one mole of IPA to produce one mole of DIPE, while in contrast, reaction (3) consumes two moles of IPA to produce one mole of DIPE. Reaction (2) is also preferred over reaction (3) on the basis of cost. The hydration reaction to produce IPA is costly as well as difficult, so it is advantageous to minimize IPA consumption in the reaction to produce DIPE. Propylene, on the other hand, is relatively low in cost since it is typically available as a by-product from other processes in a refinery.

The olefin hydration and etherification or alcohol dehydration reactions may be carried out in a single stage, or in two stages. As discussed above, the hydration reaction conditions are very different from the etherification reaction conditions, and an advantage of the two-stage design is that each stage may be independently optimized for a particular reaction. For example, U.S. Pat. No. 5,144,086 disclosed a DIPE production process using two separate reactors, the first dedicated to forming IPA by olefin hydration and the second dedicated to forming DIPE by dehydration of IPA. In this process, propylene and water are introduced to a first reactor containing an acidic hydration catalyst to produce an IPA-containing effluent that is substantially free of DIPE. After separating the effluent stream to remove the propylene and propane, the IPA-containing stream is passed to a second reactor containing a zeolite catalyst to produce an effluent that contains DIPE, water and propylene. The effluent from the second reactor is then fractionated to produce the DIPE product. It is important to note that because any propylene is removed prior to the second reactor, this process produces DIPE only by reaction (3) and not at all by reaction (2) therefore requiring two moles of IPA to be made in the first reactor for each mole of DIPE produced.

Similarly, in the DIPE production process disclosed in U.S. Pat. No. 4,935,552, propylene, water, and IPA are introduced to a first reactor containing a hydration/etherification catalyst to form an effluent which consists of IPA, DIPE, and unconsumed reactants. The effluent is then flashed to remove any propylene and extracted with water to transfer the IPA to the aqueous phase. A portion of the resulting hydrocarbon phase containing high purity DIPE is recycled to the first reactor in order to control the temperature. The aqueous IPA phase is passed to a second reactor, which is a catalytic distillation unit, where dehydration of the IPA to form DIPE takes place. It is important to note that in this second reactor, DIPE is made exclusively by reaction (3) since the propylene has all been removed. Consequently, the first reactor must provide two moles of IPA for every mole of DIPE produced.

Applicants' invention for the production of DIPE addresses the prior art drawback of high IPA consumption. Applicants' invention reduces production costs through more efficient use of the IPA produced in the hydration zone by optimizing the etherification zone to produce DIPE according to reaction (2) instead of exclusively by reaction (3). Additionally, applicants' invention increases DIPE product yield beyond thermodynamic equilibrium limitations and consolidates separation equipment through performing the etherification by catalytic distillation.

SUMMARY OF THE INVENTION

An object of the present invention is to develop a process for the efficient production of diisopropyl ether where catalytic distillation is used to increase the yield of product beyond thermodynamic equilibrium limitations. The invention comprises, in a hydration zone, reacting the propylene in a feedstock with water in the presence of a catalyst and an optional organic cosolvent to effect hydration to produce an effluent stream containing at least water, unreacted propylene, and isopropyl alcohol, and then, in an etherification zone, further reacting at least a portion of the effluent stream by catalytic distillation in the presence of a catalyst to effect the reaction of propylene and isopropyl alcohol to form DIPE while concurrently separating an organic portion and an aqueous portion, and collecting the organic portion containing the diisopropyl ether.

A specific embodiment of the invention is one where the organic portion is further separated within the catalytic distillation zone by distillation, condensation, or adsorption, into a diisopropyl ether rich portion and a propylene rich portion, and the diisopropyl ether is recovered from the diisopropyl ether rich portion. Another specific embodiment of the invention is one where the catalyst in the hydration zone is a strongly acidic cation exchange resin. Another specific embodiment of the invention is one where the catalyst in the etherification zone is a strongly acidic cation exchange resin. A more specific embodiment is one where a portion of the effluent stream is recycled to the hydration zone. Yet another more specific embodiment is one where an organic cosolvent is added to the hydration zone.

BRIEF DESCRIPTION OF THE DRAWING

The FIGURE is a much simplified, non-detailed process flow scheme of one embodiment of the present invention.

DETAILED DESCRIPTION OF THE INVENTION

In general terms, the first stage of the present invention involves a propylene-containing hydrocarbon feedstock being contacted with water in a hydration zone in the presence of a hydration catalyst under hydration conditions to produce a hydration zone effluent stream containing at least water, unreacted propylene, and IPA.

The propylene-containing hydrocarbon feedstock may be a refinery $C_3$ hydrocarbon stream containing at least propylene and, most likely, a mixture of propylene and propane. Suitable sources for the propylene-containing hydrocarbon feedstock include, but are not limited to, gas plant off-gas containing propylene, naphtha cracker off-gas containing light olefins, and refinery fluidized catalytic cracked (FCC) propane/propylene streams. It is preferred that the hydrocarbon feedstock have a propylene concentration in the range of about 50 to about 92 mole %. Increasing the propylene purity of the hydrocarbon feedstock will increase DIPE yield and can be accomplished through fractionation or any other processes known to those skilled in the art. However, the additional process steps to increase the propylene purity of the hydrocarbon feedstock may increase the overall cost of the process.

The hydration catalyst may be any known hydration catalyst including, but not limited to, ion exchange resins and zeolite catalysts. These catalysts are well known in the art and do not require extensive discussion. The preferred catalyst is a strongly acidic cation exchange of the sulfonic acid-type resin derived from styrene, phenolsulfonic acid-type resin and the like. The sulfonic acid type ion exchange resin derived from styrene is obtained by copolymerizing styrene with a polyunsaturated compound such as divinylbenzene to thereby yield a resin, and then sulfonating the resin. A common strongly acidic cation exchange resin is Amberlyst-36 marketed by Rohm and Haas. Examples of cation exchange resin catalysts such as this being used for the hydration of propylene include U.S. Pat. Nos. 4,352,945, 4,469,905 and 4,579,984. Shape-selective acidic zeolite catalysts may also be used as hydration catalysts. Two categories of zeolites are useful, namely the intermediate pore size variety, for example, ZSM-5, and the large pore size variety as represented by, for example, Y, Beta and ZSM-12 zeolites. Examples of zeolitic catalysts such as these being used in hydration applications include U.S. Pat. Nos. 4,214,107, 4,906,787, 4,499,313.

Suitable hydration conditions include a temperature of about 50° to about 450° F., preferably about 280° to about 350° F., a pressure of about 500 to about 1600 psig, preferably 1000 to about 1500 psig, and a water to olefin ratio of about 0.1:1 to about 30:1, preferably about 0.5:1 to about 5:1. The hydration may be carried out in the liquid phase, vapor phase or mixed vapor-liquid phase conditions in a batch or continuous manner. With respect to the reactor, a stirred tank or fixed bed reactor may be employed. The flow of reactants and products may be trickle-bed, liquid-upflow, liquid-downflow, countercurrent, or cocurrent. A suitable liquid hourly space velocity is about 0.1 to about 20, preferably about 0.1 to about 2 when operating in the continuous mode. The preferred embodiment of the hydration zone is a fixed bed operating in the continuous mode. A suitable method and reactor for operating the hydration zone is described in U.S. Pat. Nos. 4,281,206 and 4,579,984.

While the reaction of propylene and water to form IPA is the main purpose of the hydration zone, it is likely that some etherification will also take place and the hydration zone effluent may be expected to contain some DIPE. The catalyst and process conditions of the hydration zone are optimized for the hydration reaction, therefore, the amount of etherification reaction will be minimal. It is contemplated, however, that the first stage may be optimized to carry out both the hydration and etherification reactions.

At least a portion of the effluent stream from the hydration zone is then passed to a catalytic distillation etherification zone. Within the catalytic distillation etherification zone propylene and IPA are catalytically reacted to form DIPE with concurrent separation and removal of the product DIPE and unreacted components. It is expected that some olefin hydration may also occur in this zone, but the primary desired reaction is etherification. The effluent from the hydration zone is introduced into the catalytic distillation unit in the vicinity of the etherification catalyst which may be any known etherification catalyst including, but not limited to, ion exchange resins and zeolite catalysts. These catalysts are well known in the art and do not require extensive discussion. Suitable cation exchange resin catalysts and zeolitic catalysts are the same as previously discussed. Like the hydration catalyst, the preferred etherification catalyst is a strongly acidic cation exchange resin of the sulfonic acid-type resin derived from styrene, phenolsulfonic acid-type resin and the like. Examples of these catalysts in etherification applications include U.S. Pat. Nos. 5,200,059 and 4,182,914 using resin catalysts, and U.S. Pat. Nos. 5,144,086 and 4,857,664 using zeolitic catalysts. Because in the present invention the etherification and hydration zones are separate, the etherification catalyst may be specifically chosen to suit etherification conditions rather than hydration conditions. It is also contemplated that, for some applications, the etherification catalyst and the hydration catalyst may be identical; preferably both are the same cation exchange resin, but they may be the same zeolitic catalyst.

As the effluent contacts the etherification catalyst, the etherification reaction takes place, and the operating conditions are optimized so the etherification proceeds mainly according to reaction (2), and to a lesser extent by the dehydration reaction (3) thereby consuming the reactants in a more efficient and economical manner. Suitable catalytic distillation etherification conditions include a temperature of about 250° to about 500° F., preferably, about 250° to about 280° F., a pressure of about 1 to about 600 psig, preferably about 350 to about 400 psig, and an olefin to IPA ratio of about 1:1 to about 2:1. It is important to keep the olefin to isopropyl alcohol ratio in this range to minimize the dehydration reaction (3) and promote the etherification reaction (2). Therefore, additional olefin may be added either to the effluent prior to the catalytic distillation unit, or directly to the catalytic distillation unit to ensure that the olefin to IPA ratio in the catalytic distillation unit is from about 1:1 to about 2:1. A suitable liquid hourly space velocity is from about 0.1 to about 20, preferably about 0.1 to about 2 when operating in the continuous mode.

Upon formation of the DIPE product, separation by distillation begins to occur. The organic portion, mainly DIPE with unreacted propylene and perhaps propane, is separated from the aqueous portion. It is expected that the IPA will be consumed in the reaction, but any unreacted IPA present will separate into the organic portion. The aqueous portion is withdrawn from the catalytic distillation etherification zone, and if necessary, the aqueous portion may be treated to remove any impurities such as sulfurous acid and chloride, and then may be recycled to the hydration zone. The organic portion containing the diisopropyl ether may be withdrawn from the catalytic distillation zone and collected. In alternate embodiments of the invention, the organic portion may be further separated within the catalytic distillation zone by distillation, by condensation, or by adsorption into a propylene rich portion and a DIPE-rich portion which are each withdrawn from the catalytic distillation etherification zone. Any IPA present will be in the DIPE-rich portion and may be removed by water washing. Propylene may be recovered from the propylene rich portion by distillation. Any unreacted propylene and IPA may be recycled to the hydration zone or the etherification zone.

Through using catalytic distillation, the present invention provides several significant advantages. For instance, DIPE yields greater than equilibrium limitations may be achieved. Because the DIPE product is distilled away from the reaction as soon as it is formed, the thermodynamic equilibrium characteristic of a static system is no longer a limiting factor and DIPE will continue to form and most of the IPA will be reacted. Furthermore, utility costs are conserved because of the efficient integration of the heat of reaction with the energy required for the distillation. Finally, IPA consumption is controlled through optimizing the operating conditions so that the etherification proceeds primarily according to reaction (2) and not exclusively by reaction (3).

There are two significant optional variations to the above-described process. In a first variation, a portion of the effluent from the hydration zone may be recycled to the hydration zone. Usually this option is used to aid in controlling the temperature of the hydration zone. In a second variation, a cosolvent is introduced into the hydration zone in addition to the olefinic hydrocarbon feedstock and the water. The purpose of the cosolvent is to enhance the solubility of propylene and thereby increase the overall conversion of propylene and water into IPA. Examples of suitable cosolvents include sulfolane, diethylene glycol dimethyl ether, and IPA. Cosolvents which do not react in the process will be carried through the flowscheme and collected in either the organic portion or the aqueous portion, depending upon the cosolvent. For example, excess IPA will be collected in the DIPE-rich portion, while sulfolane and diethyl glycol dimethyl ether will be collected in the aqueous portion. When the cosolvent is IPA, the IPA may be removed from the DIPE-rich portion using common separation techniques such as water washing, and then may be recycled to the hydration zone. When the cosolvent is sulfolane or diethyl glycol dimethyl ether, the cosolvent may simply remain in the aqueous portion and be recycled with the water to the hydration zone.

Without intending any limitation of the scope of the present invention, and as merely illustrative, the invention is explained below in specific terms as applied to a specific embodiment of the invention which is based on a design for a commercial scale unit. Referring to the FIGURE, water is fed into hydration zone 4 via line 2 at a flow rate of 3200 lb moles/hr. A propylene-containing feedstock enters into hydration zone 4 via line 6 at a flow rate of 1608 lb moles/hr.

The feedstock is a mixture of propylene and propane which contains 70 mole % propylene. Passing the propylene-containing feedstock of line 6 to a fractionation column (not shown) to remove propane from the system may increase the purity of the propylene. In hydration zone 4, water is reacted with propylene to produce IPA in the presence of Amberlyst-36. The hydration reaction conditions include a temperature of about 300° F. and a pressure of about 1500 psia. The hydration reaction zone effluent conducted in line 8, which has an approximate composition of 19% propane, 4% propylene, 21% water, 10% DIPE, 46% IPA, is fed into catalytic distillation etherification zone 10. Additional propylene is fed to catalytic distillation etherification zone 10 through line 22 so that the combined olefin to alcohol ratio of the two feeds in lines 8 and 22 is about 1.2:1.

In catalytic distillation etherification zone 10, propylene is reacted with IPA to form DIPE in the presence of the Amberlyst-36. The etherification reaction conditions include a temperature of about 220° F. and a pressure of about 400 psia. Also in catalytic distillation etherification zone 10, an organic portion and an aqueous portion are separated by distillation. The aqueous portion is removed from catalytic distillation etherification zone 10 via line 14. The aqueous portion may be treated by, for example, passing over a solid adsorbent to remove impurities such as sulfurous acid and chloride (not shown) and then recycled to the hydration zone 4 via optional line 20. The organic portion is further distilled within catalytic distillation etherification zone 10 into a DIPE-rich portion and a propylene rich portion. The DIPE-rich portion is removed from catalytic distillation etherification zone 10 via line 24. IPA, if present, may be removed from the DIPE-rich portion by water washing (not shown). The propylene rich portion is removed from catalytic distillation etherification zone 10 via line 12. Propylene may be recovered from the propylene rich portion by further distillation (not shown). Unreacted water and propylene may be recycled to hydration zone 4.

A significant optional variation includes recycling a portion of the effluent conducted in line 8 to the hydration zone via optional line 16 in order to help control the temperature in hydration zone 4 and act as a solvent to increase hydration. Another optional variation includes introducing a cosolvent, such as sulfolane, to hydration zone 4 via optional line 18 to enhance the propylene solubility and increase hydration. It must be emphasized that the above description and variations are merely illustrative of embodiments and are not intended as undue limitations on the generally broad scope of the invention. For example, one skilled in the art would readily understand how to further separate the organic portion within the catalytic distillation zone into a DIPE-rich portion and a propylene rich portion using condensation or adsorption.

What is claimed is:

1. A process for producing diisopropyl ether comprising the steps of:

a. reacting in a hydration zone operating at a temperature from about 50° F. (10° C.) to about 400° F. (204° C.) and a pressure from about 500 to about 1600 psig the propylene in a feedstock with water in the presence of a first catalyst selected from the group consisting of acidic cation exchange resins and acidic zeolites, and an optional organic cosolvent, to effect hydration of the propylene to produce an effluent stream containing at least water, unreacted propylene, and isopropyl alcohol;

b. reacting in a catalytic distillation etherification zone operating at a temperature from about 250° F. (121° C.)

to about 500° F. (260° C.) and a pressure from about 1 to about 600 psig at least a portion of the effluent stream and sufficient propylene to provide a propylene to isopropyl alcohol ratio of about 1:1 to about 2:1 in the presence of a second catalyst selected from the group consisting of acidic cation exchange resins and acidic zeolites to effect reaction of propylene and isopropyl alcohol to form diisopropyl ether and concurrently separating an organic portion containing the diisopropyl ether and an aqueous portion; and c. collecting the organic portion containing the diisopropyl ether.

2. The process of claim 1 further comprising separating by distillation within the catalytic distillation zone, the organic portion into a diisopropyl ether rich portion and a propylene rich portion, and recovering the diisopropyl ether from the diisopropyl ether rich portion.

3. The process of claim 1 further comprising separating by condensation within the catalytic distillation zone, the organic portion into a diisopropyl ether rich portion and a propylene rich portion, and recovering the diisopropyl ether from the diisopropyl ether rich portion.

4. The process of claim 1 further comprising separating by adsorption within the catalytic distillation zone, the organic portion into a diisopropyl ether rich portion and a propylene rich portion, and recovering the diisopropyl ether from the diisopropyl ether rich portion.

5. The process of claim 1 where the reaction occurs in the presence of an optional organic cosolvent selected from the group consisting of sulfolane, diethylene glycol dimethyl ether, and isopropyl alcohol.

6. The process of claim 1 where the first and second catalysts are identical and are a strongly acidic cation exchange resin.

7. The process of claim 1 where the feedstock comprises a propylene and propane mixture containing from about 50 to about 92 mole % propylene.

8. The process of claim 1 where the aqueous portion is recycled to the hydration zone.

9. The process of claim 8 where the aqueous portion is treated to remove sulfurous acid or chloride prior to being recycled to the hydration zone.

10. The process of claim 2 where the diisopropyl ether rich portion is water washed to remove isopropyl alcohol, affording an aqueous isopropyl alcohol stream.

11. The process of claim 10 where the aqueous isopropyl alcohol stream is recycled to the hydration zone.

12. The process of claim 10 where the aqueous isopropyl alcohol stream is recycled to the catalytic distillation etherification zone.

13. The process of claim 3 where the diisopropyl ether rich portion is water washed to remove isopropyl alcohol, affording an aqueous isopropyl alcohol stream.

14. The process of claim 13 where the aqueous isopropyl alcohol stream is recycled to the hydration zone.

15. The process of claim 13 where the aqueous isopropyl alcohol stream is recycled to the catalytic distillation etherification zone.

16. The process of claim 4 where the diisopropyl ether rich portion is water washed to remove isopropyl alcohol, affording an aqueous isopropyl alcohol stream.

17. The process of claim 16 where the aqueous isopropyl alcohol stream is recycled to the hydration zone.

18. The process of claim 16 where the aqueous isopropyl alcohol stream is recycled to the catalytic distillation etherification zone.

* * * * *